United States Patent [19]

Sogawa et al.

[11] Patent Number: 5,086,786
[45] Date of Patent: Feb. 11, 1992

[54] ELECTRODE DEVICE FOR HEATING TUMOR IN ENDOTRACT ORGAN

[75] Inventors: Akira Sogawa, Tokyo; Kiyoshi Kitagawa, Chiba; Chikau Onodera, Tokyo; Tadashi Onuma, Kukizaki, all of Japan

[73] Assignee: Kureha Kagaku Kogyo Kabushiki Kaisha, Tokyo, Japan

[21] Appl. No.: 493,429

[22] Filed: Mar. 14, 1990

Related U.S. Application Data

[63] Continuation-in-part of Ser. No. 337,138, Apr. 12, 1989, abandoned, which is a continuation-in-part of Ser. No. 64,574, Jun. 22, 1987, abandoned.

[30] Foreign Application Priority Data

Jun. 27, 1986 [JP] Japan .................................. 61-98429
Jun. 27, 1986 [JP] Japan .................................. 61-98430

[51] Int. Cl.$^5$ .............................................. A61N 1/00
[52] U.S. Cl. ...................................... 128/783; 128/784; 128/798; 128/804
[58] Field of Search ............... 128/798, 802, 804, 783, 128/784, 788

[56] References Cited

U.S. PATENT DOCUMENTS

| | | | |
|---|---|---|---|
| 1,975,518 | 10/1934 | Rose | 128/804 X |
| 3,746,004 | 7/1973 | Jankelson | 128/798 |
| 4,140,130 | 2/1979 | Storm | 128/798 |
| 4,378,806 | 4/1983 | Henley-Cohn | 128/804 |
| 4,646,756 | 3/1987 | Watmough et al. | 128/804 |
| 4,676,258 | 6/1987 | Inokuchi et al. | 128/804 |
| 4,708,149 | 11/1987 | Axelgaard et al. | 128/802 |
| 4,887,614 | 12/1989 | Shirakami et al. | 128/804 |

FOREIGN PATENT DOCUMENTS

| | | | |
|---|---|---|---|
| 0115420 | 8/1984 | European Pat. Off. | |
| 0139433 | 5/1985 | European Pat. Off. | |
| 0205384 | 12/1986 | European Pat. Off. | 128/784 |
| 0248758 | 12/1987 | European Pat. Off. | 128/804 |
| 0889010 | 12/1981 | U.S.S.R. | 128/804 |

OTHER PUBLICATIONS

Brezovich et al., "A Practical System for Clinical Radio Frequency Hyperthermia", Int. J. Rad. Oncology Biol. Phys., vol. 7, No. pp. 423–430, 3/1981.

*Primary Examiner*—Edward M. Coven
*Assistant Examiner*—Jessica J. Harrison
*Attorney, Agent, or Firm*—Oblon, Spivak, McClelland, Maier & Neustadt

[57] ABSTRACT

An electrode device for heating a tumor in an endotract organ by high frequency convergent electric current has a container of a flexible polymeric material provided with thick side wall, a thick bottom wall connected to one end of the side wall and an opening defined by the other end of the side wall. The device further has a deformable electrode member disposed near an inner surface of the thick bottom wall, and a flexible polymeric film fluid-tightly attached to the other end of the thick side wall. A mesh-like member of a flexible polymeric material is disposed between the electrode member and the flexible polymeric film, and has a plurality of first passages leading to a top surface thereof and a bottom surface thereof, and a plurality of second passages each communicating the first passages with each other.

15 Claims, 6 Drawing Sheets

ELECTRODE DEVICE FOR HEATING TUMOR IN ENDOTRACT ORGAN

CROSS-REFERENCE TO RELATED APPLICATION

The present application is a continuation-in-part of application Ser. No. 337,138 filed on Apr. 12, 1989, now abandoned, which is a continuation-in-part of application Ser. No. 064,574 filed on Jun. 22, 1987, now abandoned.

BACKGROUND OF THE INVENTION

1. Field of the Invention

This invention concerns a heating electrode device for medical use and, particularly, it relates to a high-frequency heating electrode device for medical use that can be applied to the hyperthermia of tumor, etc.

2. Description of the Related Art

High-frequency hyperthermia has been known in which therapy is carried out by applying heat to a lesional portion of a patient, utilizing the fact that cancer cells, etc. are less resistant to heat than normal cells.

In the conventional high-frequency heating method, hyperthermia is carried out by putting a region including an aimed portion to be heated of a living body between two opposed plate-like electrodes and applying a high-frequency current between the electrodes from a high-frequency generator.

In this case, because of the difference in electrical constants (electroconductivity and dielectric constant) between a subcutaneous fat layer and an endotract organ tissue, the subcutaneous fat layer tends to be heated more intensely, or a patient may complain of undesirable feeling of heat, or the epidermal tissue may suffer from burns due to the intense heating at a portion near the electrode body. Accordingly, there has been proposed a method of attaching a flexible and gastight bag member between a living body and electrode body and filling or circulating a coolant into or through the inside of the bag member. However, although there is no trouble so long as the device operates normally, if any unexpected accident should occur such as change of the introduction pressure, interruption or leakage of a coolant, the electrode body may possibly be brought into a close contact with the living body thereby causing an anxiety in view of the safety. In addition, it is generally necessary to provide the electrode device of this type with an additional device for securing the electrode device to the intended portion to be heated at the inside or the outside of the living body.

SUMMARY OF THE INVENTION

It is therefore an object of the present invention to provide an electrode device for heating tumor in endotract organ, which is capable of safely heating a rugged surface of endotract lesion to be treated even if the electrode device is arranged on said rugged surface in such a manner that the protruding portion of the endotract lesion is projected into an interior of the electrode device.

In accordance with the present invention, the foregoing object can be attained by an electrode device for heating tumor in an endotract organ by high frequency convergent electric current, which is deformable and insertable into said endotract organ, comprising: a container made of a flexible polymeric material, and having a thick side wall, a thick bottom wall connected to one end of the side wall and an opening defined by the other end of the side wall; a deformable electrode member disposed near an inner surface of the thick bottom wall for flowing the electric current into a living body in association with another electrode member which is located on an outer surface of the living body; a cable fluid-tightly piercing the side wall, one end of which is electrically connected to the electrode member to supply a high frequency current to the electrode member; a flexible polymeric film fluid-tightly attached to the thick side wall to close the opening; a unit connected to the container for supplying and discharging a coolant into and out of a space defined by the thick side wall, the thick bottom wall and the flexible polymeric film; and a mesh-like member of a flexible polymeric material disposed between the electrode member and the flexible polymeric film, and having a plurality of first passages leading to a top surface thereof and a bottom surface thereof, and a plurality of second passages each communicating the first passages with each other.

According to the present invention, since the electrode device comprises a mesh-like member of a flexible polymeric material disposed between the electrode member and the flexible polymeric film, and having a plurality of first passages leading to a top surface thereof and a bottom surface thereof, and a plurality of second passages each communicating the first passages with each other, even if the flexible polymeric film is pressed by a leading end of the protruding portion of endotract lesion causing a pressed portion of the flexible polymeric film to contact with the mesh-like member, the coolant can still flow through a region of the mesh-like member, which region is sandwiched between the pressed portion of the flexible polymeric film and the electrode member, to thereby cool efficiently the leading end of the protruding portion as well as the pressed portion of the flexible polymeric film.

Accordingly, the electrode device of the present invention makes it possible to treat the rugged endotract lesion with great safety.

Further objects and advantages of the present invention will be apparent from the following description of the preferred embodiments of the invention as illustrated in the accompanying drawings.

DESCRIPTION OF THE PREFERRED EMBODIMENTS

Figure 1:
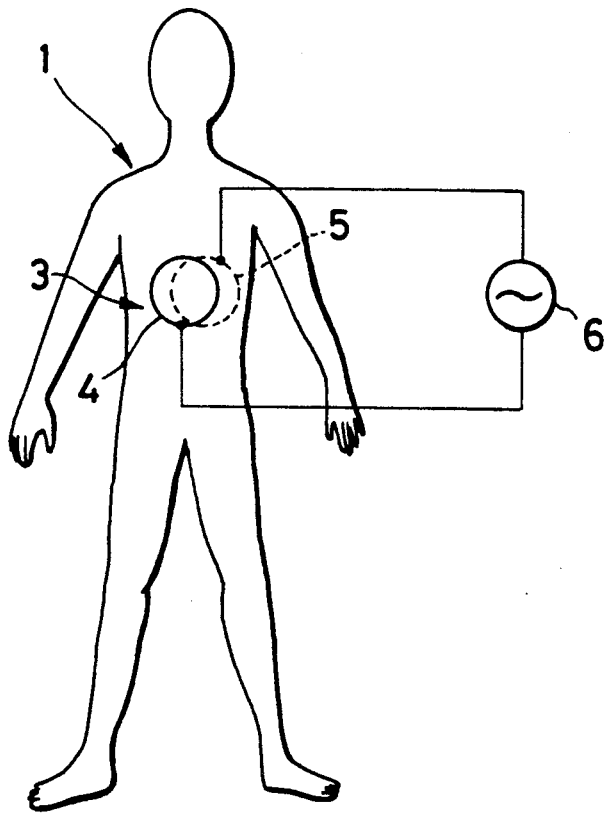
FIGS. 1 and 2 are explanatory views of conventional high-frequency hyperthermia.
Figure 2:
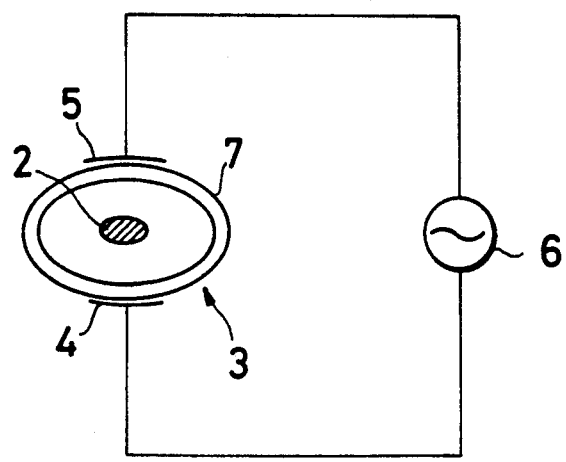

In the conventional high-frequency heating method, hyperthermia is carried out as shown in FIGS. 1 and 2, by putting a region 3 including an aimed portion 2 to be heated of a living body 1, which has subcutaneous fat layer 7, between two opposed plate-like electrodes 4 and 5 and applying a high-frequency current between the electrodes 4 and 5 from a high-frequency generator 6.

Figure 3A:
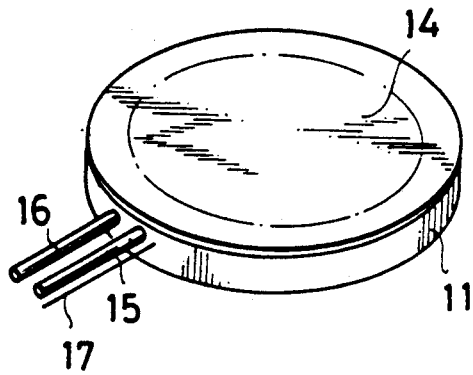
FIGS. 3a and 3b are detailed explanatory views illustrating one embodiment of the electrode device according to the present invention.
Figure 3B:
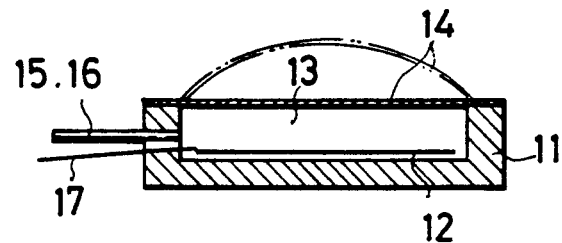

In FIGS. 3a and 3b, a thick walled container 11 is made of a flexible polymeric material such as synthetic or natural rubber of excellent adaptability with the shape of a living body to be applied, for example, silicone rubber. The shape and the size of the container 11 may optionally be designed in accordance with the purpose of use. For example, in a case of an electrode device for vagina, it may be a flat elliptic shape having outer diameter of 30-90 mm, wall thickness of 8-25 mm and depth of 5-15 mm in view of easy installation and withdrawal. An electrode member 12 is disposed to the inner surface of the container 11 on the side opposite to the opening of the container. The electrode member 12 is made of highly electroconductive material such as copper or silver and can be formed, for example, in an easily deformable plate-like, foil-like or mesh-like shape. The shape of the electrode member is not necessarily dependent upon the outer shape of the container 11. The electrode member 12 is electrically connected with a conductor 17 which passes through the wall of the container and is connected with a high-frequency generator (not illustrated). The opening of the container 11 is closed by a flexible polymeric film 14 so as to form a gastight space 13 within the container. The space 13 is so adapted that a coolant such as water or brine can be filled into or circulated through supplying and discharging channels 15 and 16 disposed to the container 11 from coolant charging and discharging means (not illustrated). The coolant is used for the purpose of preventing the localized heating, as well as for firm contact of the electrode device with the aimed portion upon hyperthermia. For effectively attaining the purpose of using the coolant, the flexible polymeric film 14 can include, for example, an extensible or expandable polymeric film made of natural or synthetic rubber with the film thickness of about 0.2-0.5 mm. Further, a sensor for monitoring the heated state may previously be disposed on the outer surface of the polymeric film 14 if required.

Figure 4:
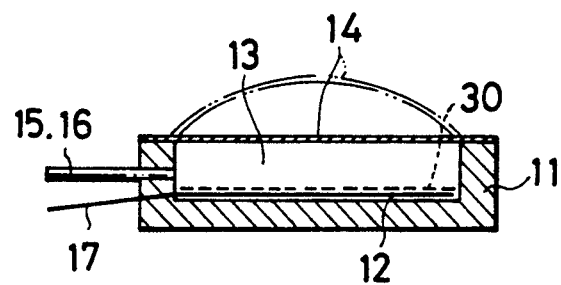
FIG. 4 is a detailed explanatory view illustrating another embodiment of the electrode device according to the present invention.
Figure 5A:
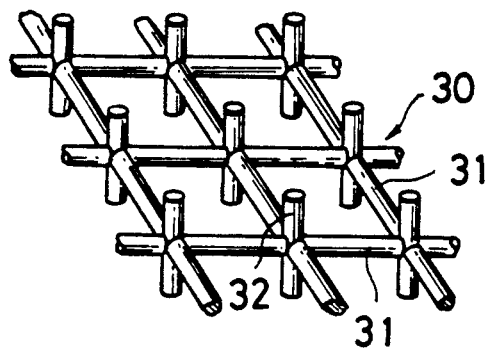
FIGS. 5a and 5b are detailed explanatory views illustrating one example of the mesh-like member to be disposed in the electrode device shown in FIG. 4.
Figure 5B:
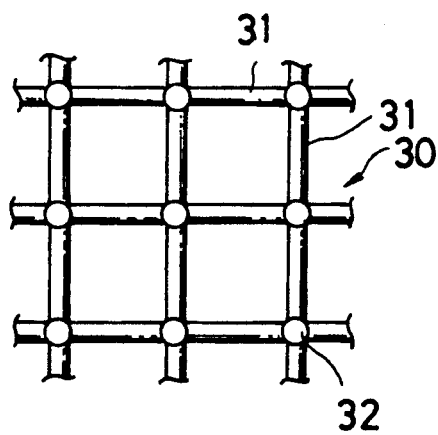

FIG. 4 shows another embodiment of the present invention. In FIG. 4, a mesh-like member 30 made of polytetrafluoroethylene is disposed near the surface of the electrode member so as to prevent the close contact between the flexible polymeric film 14 and the electrode member 12. FIGS. 5a and 5b show one example of the mesh-like member 30 represented by FIG. 4. The mesh-like member 30 is disposed near the surface of the electrode member 12 and so adapted as to permit the coolant to pass through a gap formed by the mesh-like member between the flexible polymeric film and the electrode member, even if the flexible polymeric film is pressed by the protruding portion of the living body to cause a pressed portion of the flexible polymeric film to contact with the mesh-like member. Namely, the mesh-like member 30 is made of polymeric material such as polytetrafluoroethylene or the like, and comprises a plurality of vertical members 32 connected to each of intersection portions of first and second horizontal members 31, 31 forming meshes of the mesh-like member 30 so that the respective vertical members 32 intersect a face defined by the first and second horizontal members 31, 31, extend upwardly and downwardly from the respective intersection portions, and have respectively a length capable of being received in a space defined by the thick side wall, the electrode member 12 and the flexible polymeric film 14 upon being disposed on the surface of the electrode member 12.

In the mesh-like member shown in FIGS. 5a and 5b, the respective vertical members 32 may be adapted to extend upwardly and downwardly from the respective first horizontal members 31 and the respective second horizontal members 31 without extending from the respective intersection portions.

FIGS. 6a to 6e show the other examples of the mesh-like member 30 represented by FIG. 4. The mesh-like members shown in FIGS. 6a to 6e are made of a flexible polymeric material such as polytetrafluoroethylene.

Figure 6A:
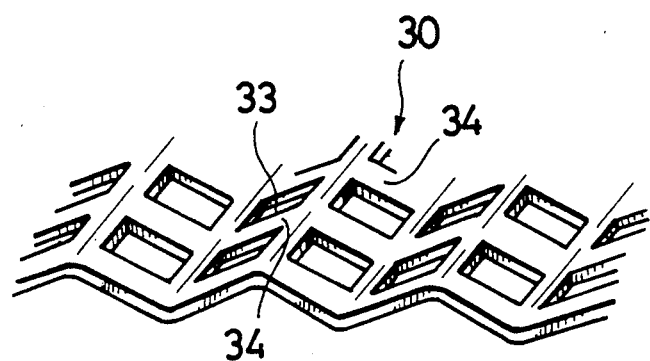
FIGS. 6a to 6e are detailed explanatory views illustrating the other examples of the mesh-like member to be disposed in the electrode device shown in FIG. 4.
Figure 6B:
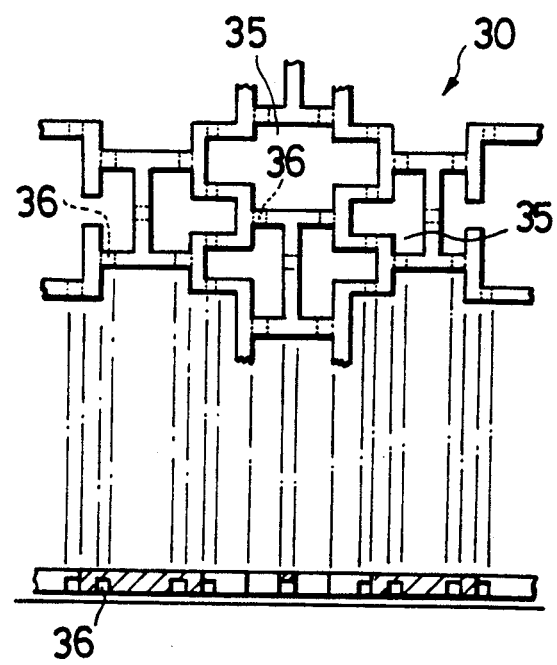

The mesh-like member 30 shown in FIG. 6a is formed in the zigzag shape. A plurality of rectangular perforation are disposed on the respective slanting surfaces 34 of the zigzag-shaped sheet member, so that a space located above the mesh-like member 30 is communicated with another space located below the mesh-like member 30 by the respective perforations 33. In the mesh-like member 30 shown in FIG. 6b, a plurality of polygonal perforations 35 are formed in a sheet member having a uniform thickness. The perforations 35 adjacent to one another are communicated with one another by passages 36 formed on the lower side of the perforated sheet member.

Figure 6C:
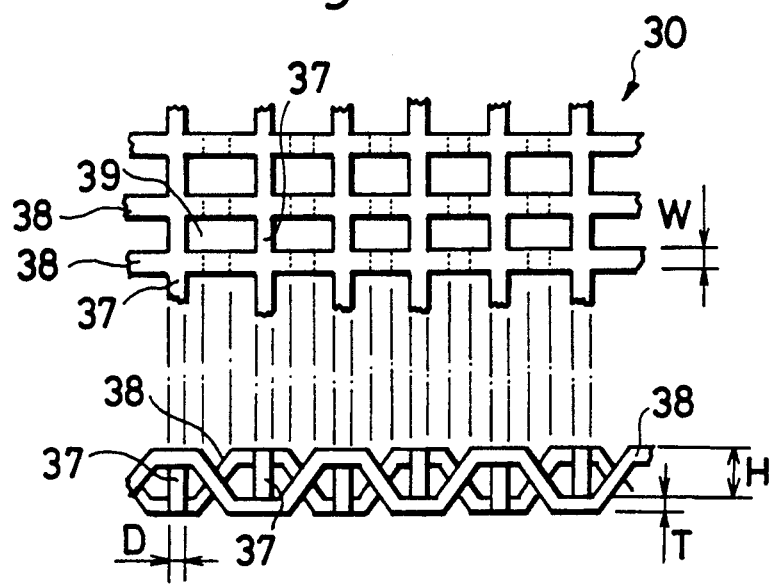

Referring to FIG. 6C, the mesh-like member 30 comprises a plurality of longitudinal elongated member 37 of thickness D and height H each formed into a corrugated shape, and a plurality of lateral elongated member 38 of thickness T and width W each formed into a corrugated shape. The longitudinal elongated member 37 are spaced apart from one another in parallel with one another in such a manner that each top portion of the longitudinal elongated member and each bottom portion of the adjacent longitudinal elongated member adjoin each other. The respective lateral elongated members 38 are so positioned that each top portion of the lateral elongated member and each bottom portion of the adjacent lateral elongated member adjoin each other, and that the respective longitudinal elongated members 37 cross the respective lateral elongated members 38. Thus, the longitudinal elongated members and the lateral elongated members are arranged to form a grating-like shape, and thereafter secured to each other at the respective crossing positions thereof. A space located above the mesh-like member 30 is communicated with another space located below the mesh-like member 30 by the respective spaces 39.

Figure 6D:
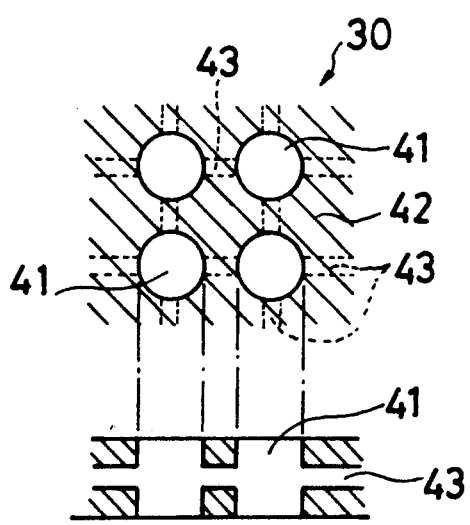

In the mesh-like member 30 shown in FIG. 6d, a plurality of perforations 41 are disposed in a sheet member 42 having a uniform thickness. Each of the perforations 41 is communicated with adjacent perforations through passages 43 extending between adjacent perforations 41.

Figure 6E:
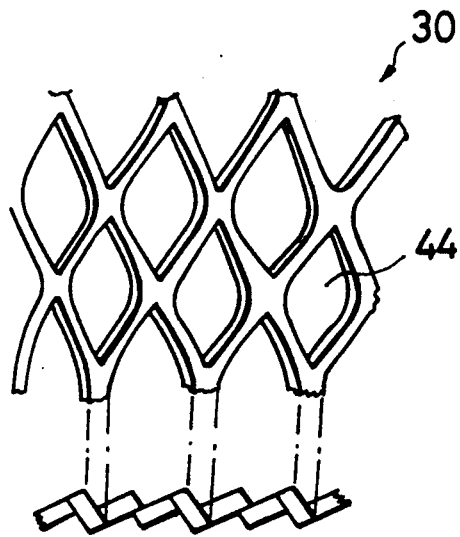

The mesh-like member 30 shown in FIG. 6e is made into a shape of an expanded member in accordance with such a method as to manufacture an expanded metal. Firstly, a plurality of rows of slit series in line are formed on a sheet member in such a manner that slits of one row are staggered relative to slits of adjacent rows. Secondly, both edge portions of the slit sheet member, which edge portions are situated along the slit series, are respectively extended in the two directions opposite to each other to thereby obtain the mesh-like member 30 shown in FIG. 6e. A space located above the mesh-like member 30 is communicated with another space located below the mesh-like member 30 by the respective perforations 44.

Figure 7A:
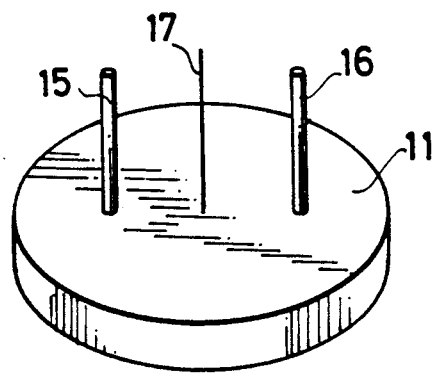
FIGS. 7a and 7b are detailed explanatory views illustrating a further embodiment of the electrode device according to the present invention.
Figure 7B:
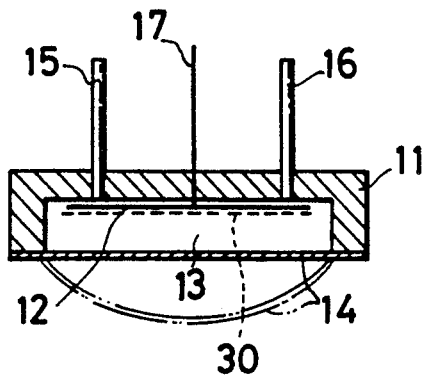

FIGS. 7a and 7b show an embodiment of an electrode device according to the present invention, which is used as the electrode device for treating cancer at the outer surface of a living body, for example, mammary cancer.

In FIGS. 7a and 7b, the coolant supplying and discharging channels 15 and 16 are disposed to the rear face of the container 11.

Figure 8:
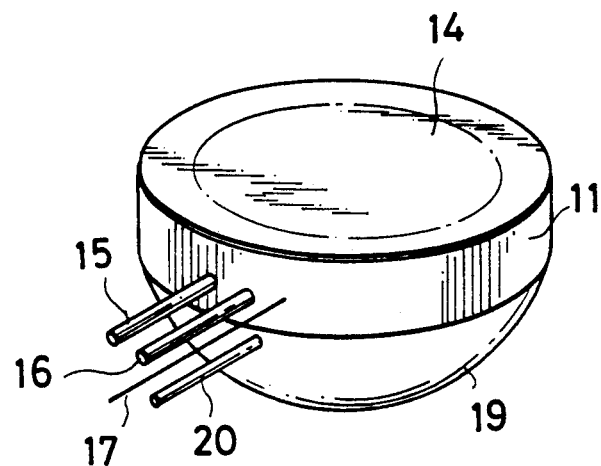
FIG. 8 is a detailed explanatory view illustrating a still further embodiment of the present invention.
Figure 9:
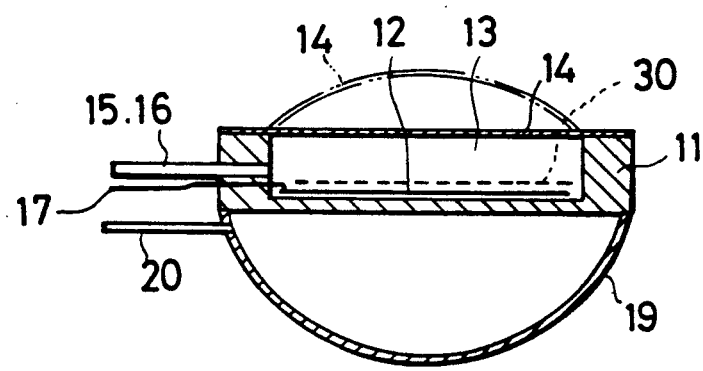
FIG. 9 is a cross-sectional view of FIG. 8.

FIGS. 8 and 9 show a further embodiment of the present invention, in which the portions identical with those in FIGS. 3a, 3b, 4, 7a and 7b carry the same reference numerals. Reference numeral 19 is a gastight bag member bonded by means of adhesives or the like to the rear face of a thick walled container 11 and adapted to supply or discharge an air or like other gas through a conduit 20. The gastight bag member 19 may be formed, for example, by shaping a flexible film or tube such as made of polyethylene or polypropylene into a predetermined configuration. However, a molding member or balloon made of silicone rubber or natural or synthetic rubber that is easily expandable or extensible with an introduced gas is preferred in that the electrode device inserted into a tubular endotract organ, for example, to the inside of a vagina can surely be secured and retained.

Although a one-path structure is illustrated for the channel for flowing gas to the inside of the gastight bag member 19 in FIG. 8 or 9, a plurality of gas flowing channels may be formed.

The electrode devices according to the present invention shown in FIGS. 3, 4 and 7 to 9 are used for high-frequency hyperthermia in combination with a counter electrode device in actual use. In this case, the temperature on the side where the electrode device according to the present invention is used can be set to a temperature optimum to the therapy by using the counter electrode device which comprises an electrode member (non-sensitive electrode) having an electrode area ten times greater than that of the electrode member of the electrode device according to the present invention. Further, in the case of actually using the electrode device shown in FIGS. 8 and 9, the electrode device is inserted into the inside of the tract of a living body in a state where the gastight bag member is deflated, and situated such that the flexible polymeric film of the thick walled container is directly faced with the aimed portion to be heated. Then, the coolant is introduced through the supplying and discharging channels 15 and 16 to the space 13. Further, air or like other gas is introduced through the conduit 20 to the gastight bag member 19 so that the electrode device is secured to the aimed portion to be heated at an appropriate pressure by utilizing the expansion of the gastight bag member 19. According to the heating electrode device of the present invention, since it is in conformity with and in close contact with the body surface and the electrode member is kept from a close contact with the living body even in a case where coolant is not present in the space within the thick walled container due to the structure in which the electrode member is disposed within the thick walled container, the hyperthermia can be conducted safely.

Further, the electrode device according to the present invention which has the gastight bag member can provide a merit that the electrode device can be secured to the aimed portion to be heated and the intrusion of the high-frequency current to the side of the gastight bag member of the thick walled container which is expanded with the gas can be decreased as little as possible.

Many widely different embodiments of the present invention may be constructed without departing from the spirit and scope of the present invention. It should be understood that the present invention is not limited to the specific embodiments described in the specification, except as defined in the appended claims.

What is claimed is:

1. An electrode device for heating a tumor of an endotract organ by high frequency current, said electrode device being deformable and insertable into said organ and comprising:

a container made of a flexible polymeric material, formed by a thick side wall and a thick bottom wall which is connected to one end of the side wall, and having an opening defined by the other end of said side wall;

a deformable electrode member disposed near an inner surface of said thick bottom wall for flowing said electric current into a living body in association with another electrode member which is located on an outer surface of said living body;

a cable fluid-tightly piercing said side wall, and connected to said electrode member at one end thereof to supply a high frequency current to said electrode member;

a flexible polymeric film fluid-tightly attached to said thick side wall to close said opening;

means connected to said container for supplying and discharging a coolant into and out of a space defined by said thick side wall, said thick bottom wall and said flexible polymeric film; and a mesh-like member of a flexible polymeric material disposed between said electrode member and said flexible polymeric film, and having a plurality of first passages leading to a top surface thereof and a bottom surface thereof, and a plurality of second passages each communicating said first passages with each other.

2. An electrode device according to claim 1 in which said mesh-like member comprises a plurality of vertical members connected to each of first and second horizontal members, which form the meshes of said mesh-like member, so that the respective vertical members intersect a surface defined by said first and second horizontal members, extend upwardly and downwardly from the respective first horizontal members and the respective second horizontal members, and have respectively a length capable of being received in a space defined by said thick side wall, said electrode member and said flexible polymeric film upon being disposed on a surface of said electrode member.

3. An electrode device according to claim 1, in which said mesh-like member comprises a sheet-like member having a plurality of polygonal perforations, and a plurality of passages formed on a lower surface of said sheet-like member for communicating said perforations with one another.

4. An electrode device according to claim 1 in which said mesh-like member comprises a sheet-like member having a plurality of perforations, and a plurality of passages formed within said sheet-like member for communicating adjacent perforations with one another.

5. An electrode device according to claim 1, in which said mesh-like member comprises a zigzag sheet-like member having on each of slanted faces thereof a plurality of perforations.

6. An electrode device according to claim 1, in which said mesh-like member comprises a plurality of longitudinal elongated members, and a plurality of lateral elongated members each having a corrugated shape and each crossing said longitudinal elongated members alternately at top and bottom portions thereof, said respective longitudinal elongated members and said respective lateral elongated members being secured to each other in said crossing portions thereof.

7. An electrode device according to claim 1, in which said mesh-like member is formed in a shape of an expanded member in accordance with a method used in producing an expanded metal.

8. An electrode device according to claim 1, which further comprises:
a flexible and gastight bag member made of an expandable material, and disposed to an outer surface of said thick bottom wall, to thereby urge said container against an aimed portion to be heated of said endotract organ when said electrode device is inserted into said endotract organ and said flexible and gastight bag member is inflated, said outer surface of said thick bottom wall being opposite to said flexible polymeric film; and
means connected to said flexible and gastight bag member for supplying and discharging a gas into and out of a space defined by said outer surface of said thick bottom wall and said flexible and gastight bag member.

9. An electrode device according to claim 8, in which said flexible and gastight bag member comprises:
a molding member or balloon made of a material selected from the group of synthetic or natural rubber, either of which is easily extensible or expandable by said supplied gas.

10. An electrode device according to claim 1, in which said flexible polymeric material for said mesh-like member comprises polytetrafluoroethylene.

11. An electrode device according to claim 1, in which the container has a flat elliptic shape with an elliptic bottom wall.

12. An electrode device according to claim 1, in which the electrode member has a plate-like shape.

13. An electrode device according to claim 1, in which said electrode member is made of a metal foil.

14. An electrode device according to claim 1, in which said electrode member has a mesh-like shape.

15. An electrode device according to claim 1, in which said flexible polymeric film is comprised of:
a material selected from the group of natural or synthetic rubber.

* * * * *

UNITED STATES PATENT AND TRADEMARK OFFICE
CERTIFICATE OF CORRECTION

PATENT NO. : 5,086,786
DATED      : February 11, 1992
INVENTOR(S): Akira Sogawa et al.

It is certified that error appears in the above-indentified patent and that said Letters Patent is hereby corrected as shown below:

On the Title page, Item[73], the Assignee should be listed as --Olympus Optical Co., Ltd., Tokyo, JAPAN--.

Signed and Sealed this

Twenty-sixth Day of April, 1994

Attest:

BRUCE LEHMAN

Attesting Officer    Commissioner of Patents and Trademarks